United States Patent [19]

Jessel, Jr. et al.

[11] Plant 4,561

[45] Jul. 1, 1980

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 10,853

[22] Filed: Feb. 9, 1979

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum cultivar particularly characterized as to uniqueness by the combined characteristics of flat capitulum form; daisy capitulum type; dark lavender pink ray floret color; diameter across face of capitulum ranging from 70 to 90 mm. at maturity; uniform nine week photoperiodic flowering response to short days; tall plant height when grown as a single stem cut spray; medium peduncle length, and minimal pollen production.

5 Drawing Figures

The present invention comprises a new and distinct cultivar of *Chrysanthemum morifolium*, Ramat., hereinafter referred to by the cultivar name Charisma.

Charisma is a product of a planned breeding program which had the objective of creating new chrysanthemum cultivars with daisy capitulum type, with lavender pink ray floret color, with eight or nine week flowering response, and with the ability to produce commercially acceptable quality in year round cut mum programs. Such traits in combination were not present in previously available commercial cultivars.

Charisma was originated from a cross made in a controlled breeding program in Barberton, Ohio in 1974. The female parent was #72245089 (unnamed seedling), a bronze daisy originated by the present inventors from a cross between Dramatic, disclosed in U.S. Plant Pat. No. 3,189, and Crackerjack (unpatented; commercially available). The male parent of Charisma was Camino Pink, disclosed in U.S. Plant Pat. No. 4,286, a lavender pink daisy. Dramatic, Crackerjack, and Camino Pink are all products of the breeding program of the present inventors.

Charisma was discovered and selected as one flowering plant within the progeny of the stated cross by Walter H. Jessel, Jr. and William E. Duffett on Nov. 19, 1975 in a controlled environment in Barberton, Ohio.

The first act of asexual reproduction of Charisma was accomplished when vegetative cuttings were taken from the initial selection in February, 1976 in a controlled environment in Barberton, Ohio, by a technician working under formulations established and supervised by Walter H. Jessel, Jr. and William E. Duffett. Horticultural examination of selected units initiated Sept. 17, 1976 has demonstrated that the combination of characteristics as herein disclosed for Charisma are firmly fixed and are retained through successive generations of asexual reproduction.

Charisma has not been observed under all possible environmental conditions. The phenotype may vary significantly with variations in environment such as temperature, light intensity, and day length. The following observations, measurements, and comparisons describe plants grown in Barberton, Ohio and Salinas, Calif. under greenhouse conditions which approximate those generally used in commercial practice.

The following traits have been repeatedly observed and are determined to be basic characteristics of Charisma which in combination distinguish this chrysanthemum as a new and distinct cultivar:

(1) Flat capitulum form.

(2) Daisy capitulum type.

(3) Dark lavender pink ray floret color.

(4) Yellow-green (immature) to yellow (mature) disc floret color.

(5) Diameter across face of capitulum ranging from 70 to 90 mm. at maturity.

(6) Uniform nine week photoperiodic flowering response to short days.

(7) Tall plant height (70 to 75 cm. for May through November flowerings from a rooted cutting planted to short days).

(8) Medium peduncle length (85 to 110 mm. for May through November flowerings from a rooted cutting planted to short days).

(9) Minimal pollen production.

The accompanying photographic drawings show typical inflorescence and foliage characteristics of Charisma, with colors being as nearly true as possible with illustrations of this type. Sheet 1 is a color photograph of Charisma as a cut spray. Sheet 2 is a black and white photograph showing three views of the capitulum of Charisma. Sheet 3 is a black and white photograph showing the foliage of Charisma at three stages of growth.

Of the many commercial cultivars known to the present inventors, the most similar existing cultivars in comparison to Charisma are Blue Marble (unpatented; commercially available) and the parental cultivar Camino Pink. Reference is made to attached Chart A which compares certain characteristics of Charisma to those same characteristics of Blue Marble and Camino Pink. General comparisions are as follows:

(1) In comparison to Blue Marble, Charisma has darker ray floret color, larger diameter across face of capitulum, taller plant height, and shorter peduncle length. The capitulum form, capitulum type, and flowering response period of Charisma are similar to those same characteristics of Blue Marble.

(2) In comparison to Camino Pink, Charisma has darker ray floret color, larger diameter across face of capitulum and taller plant height. The capitulum form, capitulum type, flowering response period, and peduncle length of Charisma are similar to those same characteristics of Camino Pink.

In the following description, color references are made to the Royal Horticultural Society Colour Chart. The color values were determined between 1:30 and 2:00 p.m. on Nov. 7, 1978 under 100 foot-candle light intensity at Salinas, Calif.

Botanical classification: *Chrysanthemum morifolium,* Ramat., cv Charisma.

INFLORESCENCE

A. Capitulum: (see Sheets 1 and 2 of drawings).
*Form.*—Flat.
*Type.*—Daisy.
*Diameter across face.*—70 to 90 mm.

B. Corolla of ray florets:
*Persistence.*—Resists shatter.
*Color (general tonality).*—Dark lavender pink, 74-C streaked over 76-D.
*Color (abaxial).*—74-B to 74-C oxidizing rapidly to 74-C streaked over 75-C.
*Color (adaxial).*—74-C streaked lightly over 75-C to 75-D.

C. Reproductive organs:
*Androecium.*—Present disc florets only; scant to numerous; scant pollen.
*Gynoecium.*—Present both ray and disc florets.

D. Corolla of disc florets:
*Color (immature).*—144-A.
*Color (mature).*—15-A.

E. Peduncle:
*Length.*—Medium, ranging from 85 to 110 mm. for a rooted cutting planted to short days for May through November flowerings.
*Color.*—Approximately 137-B overlaid with white.

PLANT

A. General appearance:
*Branching pattern.*—Semi-upright.

*Height.*—Tall, ranging from 70 to 75 cm. from a rooted cutting planted to short days for May through November flowerings.

B. Foliage: (See Sheets 1 and 3).
*Color (abaxial).*—Approximately 137-A to 137-B.
*Color (adaxial).*—Approximately 137-B overlaid with white.

CHART A

COMPARISON OF CHARISMA, BLUE MARBLE AND CAMINO PINK

| Cultivar | Ray floret color | Capitulum form and type | Diameter across face of Capitulum | Plant height | Flowering response period | Peduncle length |
|---|---|---|---|---|---|---|
| Charisma | Dark lavender pink | Flat daisy | 70 to 90 mm. | Tall, 70 to 75 cm. | 9 week | Medium, from 85 to 110 mm. |
| Blue Marble | Lavender pink | Flat daisy | 60 to 85 mm. | Medium, 60 to 65 cm. | 9 week | Long, from 150 to 200 mm. |
| Camino Pink | Lavender pink | Flat daisy | 60 to 80 mm. | Medium, 60 to 65 cm. | 9 week | Medium, from 80 to 95 mm. |

COMPARISONS MADE OF PLANTS GROWN AS SINGLE STEM CUT SPRAYS IN BARBERTON, OHIO AND IN SALINAS, CALIFORNIA.

We claim:

1. A new and distinct cultivar of *Chrysanthemum morifolium,* Ramat., plant as shown and described, known by the cultivar name Charisma and particularly characterized as to uniqueness by the combined characteristics of flat capitulum form; daisy capitulum type; dark lavender pink ray floret color; diameter across face of capitulum ranging from 70 to 90 mm. at maturity; uniform nine week photoperiodic flowering response to short days; tall plant height when grown as a single stem cut spray; medium penduncle length and minimal pollen production.

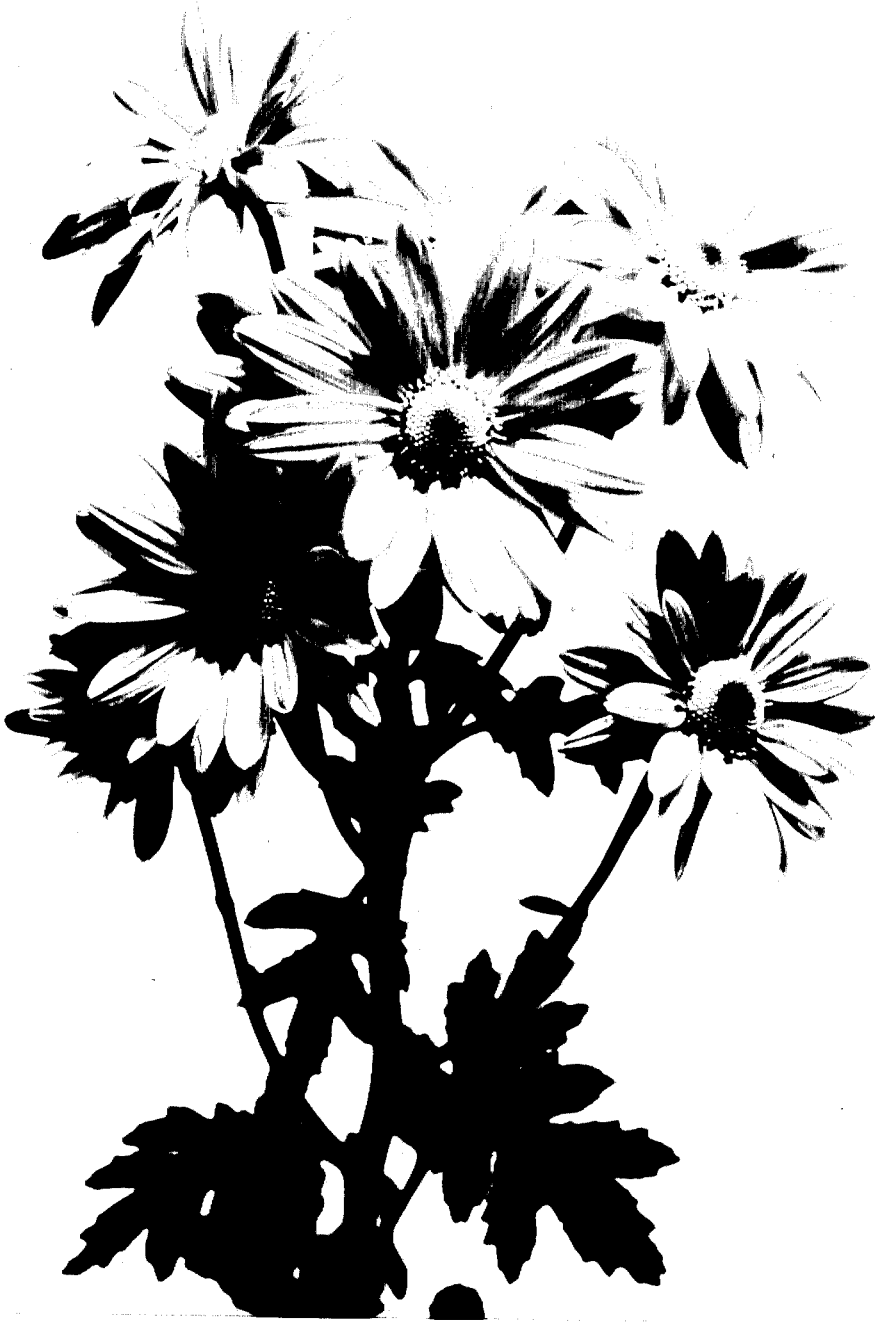

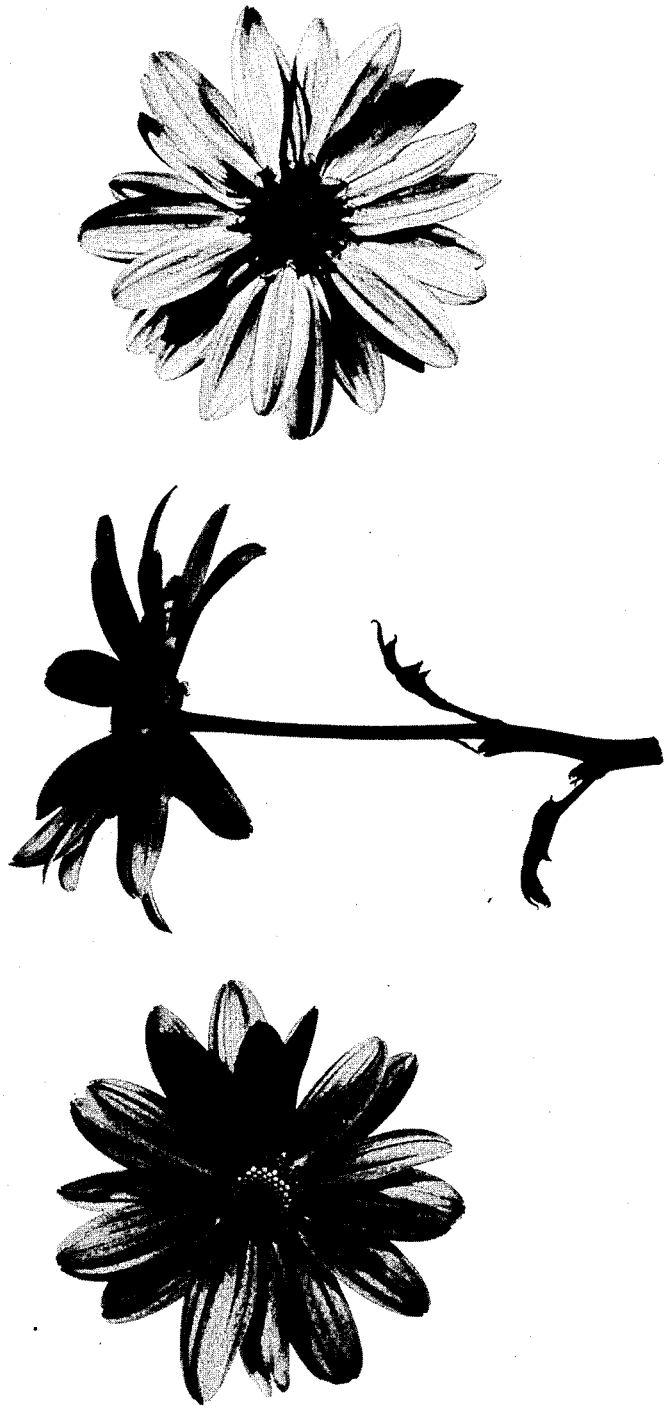

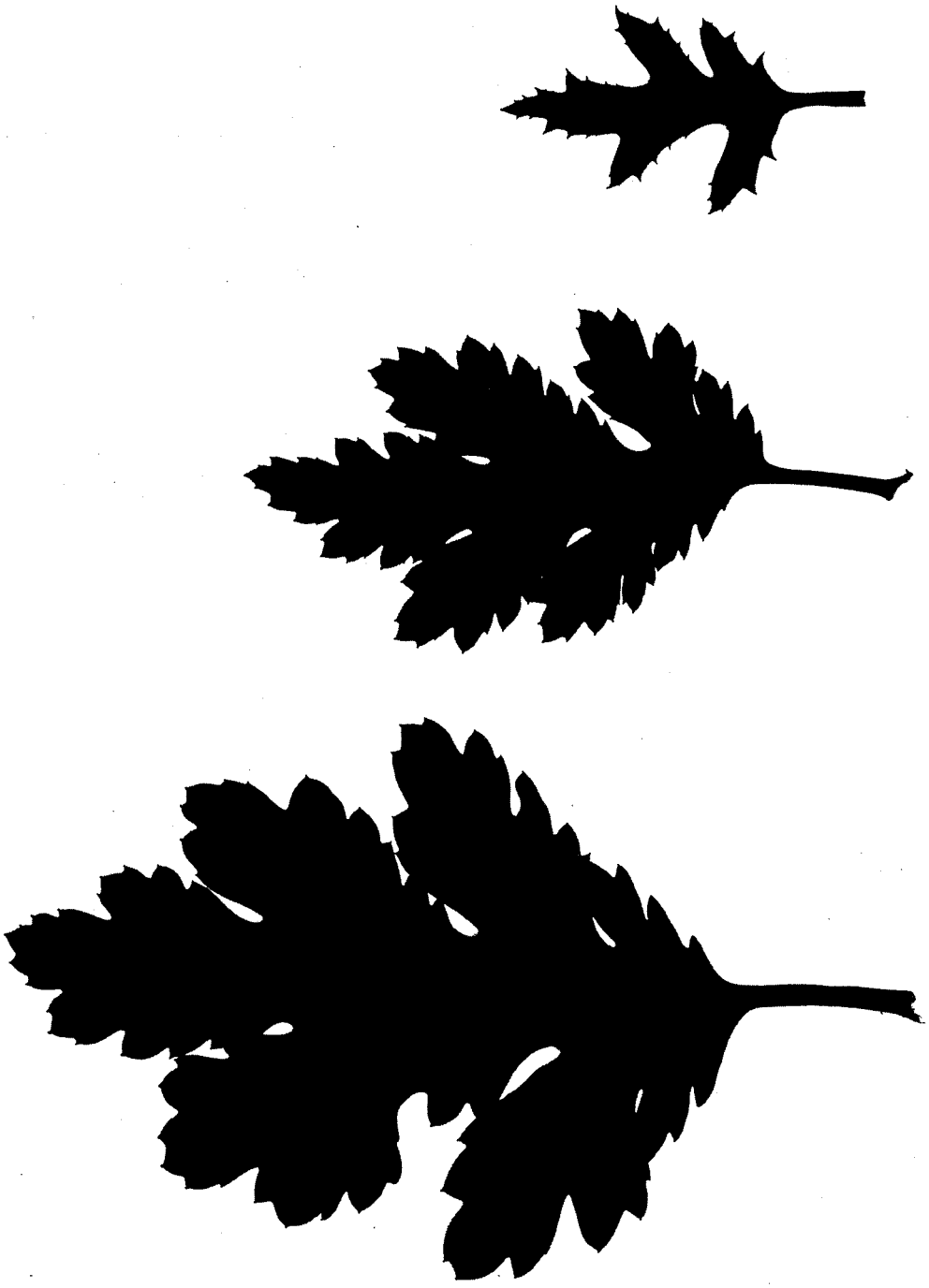

* * * * *